United States Patent [19]

Voorhees

[11] 4,018,927
[45] Apr. 19, 1977

[54] TREATMENT OF PROLIFERATING SKIN DISEASES WITH PAPAVERINE ALKALOIDS

[75] Inventor: John J. Voorhees, Ann Arbor, Mich.

[73] Assignee: The Regents of the University of Michigan, Ann Arbor, Mich.

[22] Filed: Nov. 20, 1975

[21] Appl. No.: 633,646

Related U.S. Application Data

[63] Continuation of Ser. No. 425,339, Dec. 17, 1973, abandoned, which is a continuation-in-part of Ser. No. 324,012, Jan. 16, 1973, abandoned.

[52] U.S. Cl. .............................................. 424/260
[51] Int. Cl.² ..................................... A61K 31/485
[58] Field of Search ................................... 424/260

[56] References Cited

OTHER PUBLICATIONS

Chem. Abst. 8th Collect. Index – vol. 66–75 (1967–1971), pp. 26198S & 26199S.

Primary Examiner—Sam Rosen
Attorney, Agent, or Firm—John J. Killinger; Roman Saliwanchik

[57] ABSTRACT

Pharmaceutical compositions for treatment of proliferating skin diseases, primarily psoriasis, but also atopic dermatitis, acne squamous carcinoma of the epidermis, ichthyosis, keratosis. The composition comprises a pharmaceutical carrier with a papaverine alkaloid as the active ingredient of the formula

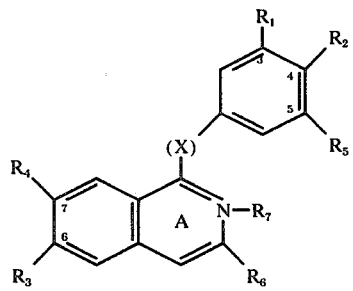

wherein
X is carbonyl or $(CH_2)_n$ and $n$ is zero or one
$R_1$ is hydroxy, methoxy, ethoxy or ethyl
$R_2$, $R_3$, and $R_4$ are hydrogen, hydroxy, methoxy or ethoxy
$R_5$ is hydrogen or ethoxy
$R_6$ is hydrogen or methyl
and $R_7$ is nothing, hydrogen or methyl and provided that when $R_7$ is hydrogen or methyl, the double bonds indicated in the A ring are saturated, including the pharmacologically acceptable acid addition salts thereof.

The compositions are administered to humans and animals topically and parenterally.

4 Claims, No Drawings

TREATMENT OF PROLIFERATING SKIN DISEASES WITH PAPAVERINE ALKALOIDS

CROSS-REFERENCE TO RELATED APPLICATIONS

This application is a continuation of application Ser. No. 425,339, filed Dec. 17, 1973, now abandoned, which is a continuation-in-part of prior copending application Ser. No. 324,012, filed Jan. 16, 1973, for "Pharmaceutical Composition and Process of Treatment" now abandoned.

BRIEF DESCRIPTION OF THE INVENTION

This invention relates to pharmaceutical compositions for application to the skin and to a method for the treatment of proliferating skin diseases. The composition may be applied topically, or by injection, intralesionally, intradermally, or sub-cutaneously. The treatment can be either therapeutic or prophylacetic.

DETAILED DESCRIPTION OF THE INVENTION

Proliferative skin diseases are widespread throughout the world and afflict millions of humans and their domesticated animals. This invention provides a method for treatment of such diseases and pharmaceutical compositions which are useful in alleviating them. As used hereinafer in this specification and in the claims, the expression "proliferative skin diseases" means benign and malignant proliferative skin diseases which are characterized by accelerated cell division in the epidermis, dermis or appendages thereto, associated with incomplete tissue differentiation. Such diseases include: psoriasis, atopic dermatitis, nor-specific dermatitis, primary irritant contact dermatitis, allergic contact dermatitis, basal and squamous cell carcinomas of the skin, lamellar ichthyosis, epidermolytic hyperkeratosis, premalignant sun induced keratosis, non-malignant keratosis, acne, and seborrhic dermatitis in humans and atopic dermatitis in domesticated animals.

Heretofore, proliferative skin diseases have been generally accepted by mankind as an ongoing evil having degrees of severity variable with time, with inherited skin traits and external factors but always have been recognized as unsightly, painful, morbid diseases. Over the history of mankind innumerable medicines and treatments have been proposed, tried and used with varying degrees of success. However, no treatment heretofore devised or pharmaceutical composition used has been entirely successful in the wide spectrum of specific diseases encompassed by the expression proliferative skin diseases.

The present day treatments of a commercial nature which are prescribed and used for the treatment of proliferative skin diseases include three approaches: (1) topical applications: coal tar derivatives, 5 fluorouracil, vitamin A acid, glucocorticoids in high dosage (constituting a non-permissive concentration), bath oils and non-specific emollient creams and ointments; (2) the systemic administration: glucocorticoids and classic anti-cancer agents, for example, methothrexate, hydroxyurea, azaribine, cyclophosphamide; (3) physical modalities: ultra violet light, x-irradiation, and in severe cases, surgery.

While these treatments provide, in certain cases, some remission of the original symptoms, each treatment suffers some defect, for example, temporary and incomplete mitigation of symptoms, rapid re-occurrence of the disease when mitigation is terminated, serious and sometimes irreversible damage (atrophy) resulting from the topical application for extended times of glucocoriticoids, acute bone marrow suppression an cirrhosis of the liver resulting from the protracted use of methothrexate which may lead to death of the patient, and the causation of cancer by the application of anti-cancer drugs, x-irradiation, or ultra violet rays.

In accordance with this invention it has been found that proliferative skin diseases are alleviated, that is, the symptoms of the disease are noticeably improved or become undetectable, by the treatment of the afflicted patient, or animal, with one or more of the pharmaceutical compositions described in detail hereinbelow.

For the purposes of this specification and the claims, a proliferative skin disease is alleviated when there is a noticeable decrease in the thickness of a lesion to palpation, with or without residual redness, or residual slightly dilated blood vessels or residual hyper- or hypo-pigmentation. For purposes of this invention and the claims hereof, psoriasis is alleviated when a scale-free psoriasis lesion is noticeably decreased in thickness, or noticeably but incompletely cleared or completely cleared.

The compositions may be applied topically or by injection, intradermally, intra- or peri-lesionally, or sub-cutaneously.

The term "topical" as employed herein relates to the use of the active ingredient incorporated in a suitable pharmacueutical carrier, and applied at the site of the disease for exertion of local action. Accordingly, such topical compositions include those pharmaceutical forms in which the compound is applied externally by direct contact with the skin surface to be treated. Conventional pharmaceutical forms for this purpose include ointments, lotions, pastes, jellies, sprays, aerosols, bath oils and the like. The term "ointment" embraces formulations (including creams) having oleaginous, absorption, water-soluble and emulsion-type bases, e.g., petroleum, lanolin, polyethylene glycols, as well as mixtures thereof. It has been found that topical application with occlusion of an area larger than the medicated area produces improved results relative to non-occluded topical applications and is, therefore, the prefered method of topical treatment with the compositions of this invention.

The percentage by w/w of the active ingredient herein utilized ranges from about 0.1% to about 15% of the pharmaceutical preparation, preferably from about 0.5% to about 2% and in these preparations the aforesaid pharmaceutical carrier for topical application constitutes a major amount of the said preparation.

Injective "intradermally" refers to positioning the composition in the high dermis by needle injection, or by high pressure air injection.

Injection "intra- or peri-lesionally" refers to positioning the composition into the lesion or into the tissue adjacent to the lesion.

The compositions may be injected so as to reach the blood stram intramuscularly, subcutaneously, intravenously, or by application to non-diseased skin.

For parenteral administration, fluid unit dosage forms are prepared utilizing the active ingredient and a sterile vehicle, water being preferred. The compound, depending on the form and concentration used, can be either suspended or dissolved in the vehicle. In preparing solutions, a water-soluble form of the compound can be dissolved in water for injection and filter sterilized before filling into a suitable vial or ampule and sealing. Advantageously, adjuvants such as a local anesthetic, preservative and buffering agents can be dissolved in the vehicle. The enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared to substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution.

The prcentage by w/v of the active ingredient for the injectable compositions ranges from about 0.1% to about 5% and preferably from about 0.5 to 2%.

The compositions of this invention may be employed in conjunction with glucocorticoids. The expression "glucocorticoids" refers to a naturally occurring product of the adrenal cortex, or a synthetic analog thereof possessing anti-inflammatory activity and minimal or no mineralocorticoid activity or sex steroid activity. Of the natural glucocorticoids, one may use for example, hydrocortisone or the synthetic glucocorticoids such as methyl prednisolone acetate (Prednisone) for oral application or triamcinolone for topical therapy. The glucocorticoids should be employed in minor amounts or "permissive dosage". The expression "permissive dosage" for glucocorticoids refers to a quantity which minimally supplements the natural output of adrenal cortical glycocorticoids in a normal person and which dosage administered, alone, has no perceptible effect on proliferative skin diseases.

The following examples describe the manner and process of making and using the invention and set forth the best mode contemplated by the inventor of carrying out the invention but are not to be construed as limiting.

EXAMPLE 1

| | | |
|---|---|---|
| Papaverine Hydrochloride | 0.9 | gm. |
| Cetyl alcohol | 5.4 | gm. |
| Stearyl alcohol | 5.4 | gm. |
| Na lauryl sulfate | 1.35 | gm. |
| White petrolatum | 27.0 | gm. |
| Propylene glycol | 9.0 | gm. |
| Distilled water q.s. | 90 | gm. |

The oil phase is prepared by melting the petrolatum, cetyl and steryl alcohols together. The remaining ingredients are dissolved in the water and added to the oil phase to form a cream.

The cream is useful in the treatment of psoriasis by rubbing on the psoriatic lesions twice a day.

EXAMPLE 2

The following topical compositions are useful in treating psoriasis.

| OINTMENT | | |
|---|---|---|
| Papaverine | 0.1 | gm. |
| Spermaceti | 27 | gm. |
| Beeswax | 27 | gm. |
| Carbapol 934 q.s. | 100 | gm. |
| CREAM | | |
| Papaverine | 1 | gm. |
| Polyethylene glycol 400 | 37.5 | gm. |
| 1,2,6-hexanetriol | 20 | gm. |
| Polyethylene glycol 4000 q.s. | 100 | gm. |
| CREAM | | |
| Papaverine Hydrochloride | 5 | gm. |
| Polyethylene glycol 400 | 37 | gm. |
| Polyethylene glycol 400 monostearate | 26 | gm. |
| Polyethylene glycol 4000 q.s. | 100 | gm. |
| CREAM | | |
| Papaverine Hydrochloride | 5 | gm. |
| Polyethylene glycol 400 | 47.5 | gm. |
| Cetyl alcohol | 5 | gm. |
| Polyethylene glycol 4000 q.s. | 100 | gm. |
| OINTMENT | | |
| Papaverine Hydrochloride | 10 | gm. |
| Anhydrous lanolin | 20 | gm. |
| Mineral Oil | 25 | gm. |
| White petrolatum q.s. | 100 | gm. |

The above ointments and creams are useful in the treatment of psoriasis by application to the affected skin areas three times a day.

EXAMPLE 3

One thousand grams of topical cream is prepared from the following types and amounts of ingredients:

| | | |
|---|---|---|
| Papaverine phosphate | 100 | gm. |
| Polysorbate 80 | 50 | gm. |
| Tegacid regular* | 150 | gm. |
| Spermaceti | 100 | gm. |
| Propylene glycol | 50 | gm. |
| Methylparaben | 1 | gm. |
| Deionized water q.s. | 1000 | gm. |

*Self-emulsifying glyceryl monostearate

The Tegacid and spermaceti are melted together at a temperature of 70°–80° C. The methylparaben is dissolved in about 500 gm. of water and the propylene glycol, polysorbate 80, and papaverine phosphate are added in turn, maintaining a temperature of 75°–80° C. The methylparaben mixture is added slowly to the Tegacid and spermaceti melt, with constant stirring. The addition is continued for at least 30 minutes with additional stirring until the temperature has dropped to 40°–45° C. Finally, sufficient water is added to bring the final weight to 1000 gm. and the preparation stirred to maintain homogeneity until cooled and congealed.

The composition is applied to human skin three times a day to treat acne.

EXAMPLE 4

Parenteral solution

A sterile aqueous solution for injection containing in 1 cc. 75 mg. of papaverine hydrochloride is prepared from the following types and amounts of materials:

| | | |
|---|---|---|
| Papaverine Hydrochloride | 50 | gm. |
| Lidocaine hydrochloride | 4 | gm. |
| Methylparaben | 2.5 | gm. |
| Propylparaben | 0.17 | gm. |
| Water for injection q.s. | 1000 | cc. |

The ingredients are dissolved in the water and the solution sterilized by filtration. The sterile solution is filled into 2 cc. vials and the vials sealed.

EXAMPLE 5

Parenteral solution

A sterile aqueous solution for injection, containing in 1 cc. 10 mg. of papaverine hydrochloride, is prepared from the following types and amounts of ingredients:

| | | |
|---|---|---|
| Papaverine Hydrochloride | 10 | gm. |
| Sodium chloride q.s. | | |
| Water for injection q.s. | 1000 | cc. |

The papaverine hydrochloride is added to the water and sufficient sodium chloride added to form an isotonic solution and the solution sterilized by filtration. The sterile solution, in the amount of 2 cc. is aseptically filled into sterile vials and sealed.

The solution is injected in 0.1 cc. quantities intradermally in the area of psoriatic lesions.

EXAMPLE 6

Following the procedure of the preceding Examples 1 to 5, inclusive, substituting an equal amount of Ethaverine, Octaverine, 1-benzyl-6,7-dimethoxyisoquinoline 3-ethyl-1-benzyl-6,7-dimethoxyisoquinoline, Papaveraldine, Codamine, Laudanine, Laudanosine, Paveril, and Norlaudanosoline for the papaverine, compositions are prepared which are useful for the treatment of psoriasis.

The compositions prepared in the preceeding examples 1 through 6, inclusive, can similarly be administered for treatment of atopic dermatitis, non-specific dermatitis, primary irritant contact dermatitis, allergic contact dermatitis, basal and squamous cell carcinomas of the skin, lamellar ichthyosis, epidermolytic hyperkeratosis, premalignant sun induced keratosis, non-malignant keratosis, acne, and seborrheic dermatitis in humans and atopic dermatitis and mange in domesticated animals.

I claim:

1. A process for treating proliferating skin diseases comprising the administration of an effective amount of a compound of the formula:

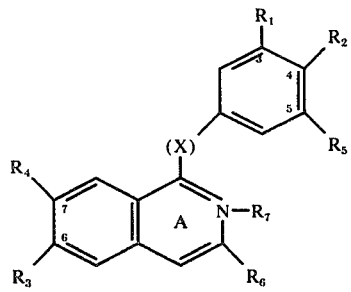

wherein X is carbonyl or $(CH_2)_n$ and $n$ is zero or one; $R_1$ is hydroxy, methoxy, ethoxy or ethyl; $R_2$, $R_3$, and $R_4$ are hydrogen, hydroxy, methoxy or ethoxy; $R_5$ is hydrogen or ethoxy; $R_6$ is hydrogen or methyl; and $R_7$ is nothin, hydrogen or methyl and provided that when $R_7$ is hydrogen or methyl, the double bonds indicated in the A ring are saturated, in association with a pharmaceutical carrier to a human or animal having a proliferating skin disease.

2. A process according to claim 1 wherein the administration is by topical application.

3. A process according to claim 1 wherein the administration is by injection.

4. A process according to claim 1 wherein the compound administered is papaverine or a pharmacologically acceptable acid addition salt thereof.

* * * * *

UNITED STATES PATENT OFFICE
CERTIFICATE OF CORRECTION

Patent No. 4,018,927    Dated April 19, 1977

Inventor(s) John J. Voorhees

It is certified that error appears in the above-identified patent and that said Letters Patent are hereby corrected as shown below:

Column 1, line 20, "prophylacetic" should read --prophylactic--; line 28, "hereinafer" should read --hereinafter--; line 34, "nor-specific" should read --non-specific--; line 39, "seborrhic" should read --seborrheic--. Column 2, line 4, "glucocoriticoids" should read --glucocorticoids--; line 5, "an" should read --and--; line 31, "pharmacueutical" should read --pharmaceutical--; line 41, "petroleum," should read --petrolatum,--; line 46, "prefered" should read --preferred--; line 54, "injective" should read --injection--; line 61, "stram" should read --stream--. Column 3, line 19, "prcentage" should read --percentage--; line 56, "steryl" should read --stearyl--. Column 6, line 25, "nothin," should read --nothing,--.

Signed and Sealed this nineteenth Day of July 1977

[SEAL]

Attest:

RUTH C. MASON
Attesting Officer

C. MARSHALL DANN
Commissioner of Patents and Trademarks